(12) United States Patent
Patel et al.

(10) Patent No.: US 12,290,499 B2
(45) Date of Patent: *May 6, 2025

(54) VIGABATRIN LIQUID PHARMACEUTICAL COMPOSITION

(71) Applicant: PYROS PHARMACEUTICALS, INC., Parsippany, NJ (US)

(72) Inventors: Nrupa Patel, Robbinsville, NJ (US); Raenel V. Gibson, Gambier, OH (US); Michael M. Smith, New York, NY (US); Edwin Urrutia, Brooklyn, NY (US)

(73) Assignee: PYROS PHARMACEUTICALS, INC., Parsippany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/759,349

(22) Filed: Jun. 28, 2024

(65) Prior Publication Data

US 2024/0398741 A1 Dec. 5, 2024

Related U.S. Application Data

(63) Continuation of application No. 18/318,697, filed on May 16, 2023, which is a continuation of application No. PCT/US2022/078202, filed on Oct. 17, 2022.

(60) Provisional application No. 63/378,383, filed on Oct. 5, 2022, provisional application No. 63/375,909, filed on Sep. 16, 2022.

(51) Int. Cl.
| | |
|---|---|
| *A61K 31/197* | (2006.01) |
| *A61J 1/14* | (2023.01) |
| *A61J 7/00* | (2006.01) |
| *A61K 9/00* | (2006.01) |
| *A61K 47/14* | (2017.01) |
| *A61K 47/26* | (2006.01) |
| *A61K 47/46* | (2006.01) |

(52) U.S. Cl.
CPC ........... *A61K 31/197* (2013.01); *A61J 1/1468* (2015.05); *A61J 7/0053* (2013.01); *A61K 9/0095* (2013.01); *A61K 47/14* (2013.01); *A61K 47/26* (2013.01); *A61K 47/46* (2013.01)

(58) Field of Classification Search
None
See application file for complete search history.

(56) References Cited

FOREIGN PATENT DOCUMENTS

| | | |
|---|---|---|
| WO | 2019/186515 A1 | 10/2019 |
| WO | WO 2020039262 A1 | 2/2020 |

OTHER PUBLICATIONS

International Preliminary Report on Patentability, received for PCT/US2022/078202, mailed Jun. 13, 2024.

*Primary Examiner* — Bethany P Barham
*Assistant Examiner* — Peter Anthopolos
(74) *Attorney, Agent, or Firm* — Mueting Raasch Group

(57) ABSTRACT

The embodiments of the present invention relate to a stable liquid vigabatrin pharmaceutical compositions in the liquid form of a solution. Particularly, the stable vigabatrin liquid pharmaceutical composition is manufactured as a ready-to-use industrialized premixture that does not require reconstitution or dilution prior to administration to a patient. The vigabatrin liquid pharmaceutical composition is stable six months or longer at room temperature and has levels of total impurities and Vigabatrin-related compound A that are both not more than 0.04% at, or prior to, six months. In some embodiments, the composition has improved stability and patient compliance. In some embodiments, the compositions may be advantageous for the patients having swallowing difficulties or when the patients are unable to take solid oral dosage forms. In some embodiments, the composition improves compliance with ketogenic diet.

19 Claims, 4 Drawing Sheets

A

VIGABATRIN
(4-aminohex-5-enoic acid)

CAS No.: 60643-86-9

Molecular Formula: $C_6H_{11}NO_2$

Molecular Weight: 129.16

B

VIGABATRIN RELATED COMPOUND A
(5-Vinylpyrrolidin-2-one)

CAS No.: 7529-16-0

Molecular Formula: $C_6H_9NO$

Molecular Weight: 111.14

INSTRUCTIONS FOR USE
SABRIL® *(SAY-bril) (vigabatrin)*
Powder for oral solution Read this Instructions for Use before your child starts taking SABRIL and each time you get a refill.

There may be new information. This information does not take the place of talking with your healthcare provider about your child's medical condition or treatment. Talk to your healthcare provider if you have any questions about the right dose of medicine to give your child or how to mix it.

IMPORTANT NOTE:
- SABRIL comes in a packet
- Each packet contains 500 mg of SABRIL powder
- SABRIL powder must be mixed with water only. The water may be cold or at room temperature.
- Your healthcare provider will tell you:
  ○ how many packets of SABRIL you will need for each dose
  ○ how many milliliters (mL) of water to use to mix one dose of SABRIL
  ○ how many milliliters (mL) of the powder and water mixture you will need for each dose of medicine
- SABRIL should be given right away after it is mixed
- Use the oral syringes, provided by the pharmacy, to measure and give the correct dose. Do not use a household teaspoon or tablespoon.

Supplies you will need to mix 1 dose of SABRIL:

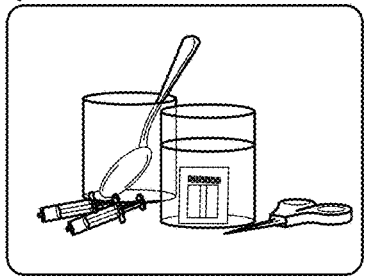

FIG. 2A

- The number of packets of SABRIL needed for each dose
- 2 clean cups: 1 for mixing and 1 for water. The cup used for mixing SABRIL should be clear so you can see if the powder is dissolved
- Water to mix with the SABRIL powder
- One small 3 mL oral syringe and one large 10 mL oral syringe, which are provided by the pharmacy
- Small spoon or other clean utensil to stir the mixture
- Scissors

Oral syringe detail

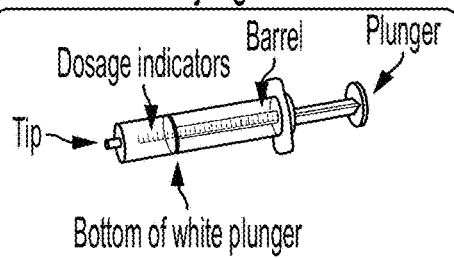

FIG. 2B

Step 1: Start with 1 of the empty cups and the total number of packets you will need for 1 dose.

Step 2: Before you open the packet, tap it to settle all the powder to the bottom of the packet.

Step 3: Use a pair of scissors to cut open the SABRIL packet along the dotted line.

Step 4: Empty the entire contents of the SABRIL packet into 1 of the clean empty cups (see FIG. 2C).

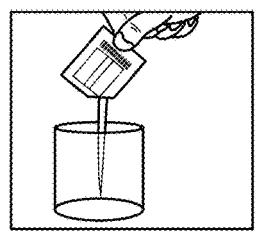

FIG. 2C

- Repeat steps 2 to 4 above to open all of the packets needed for 1 dose of SABRIL.

FIG. 2

Step 5: Take the second cup and fill it half way with water (see FIG. 2D).

Do not mix SABRIL with anything other than water.

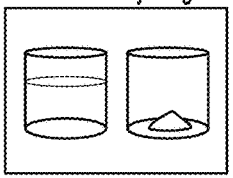

FIG. 2D

- You will use the larger oral syringe (10mL) to draw up the water needed to mix with the powder from the packets. You will need 10 mL of water for each packet of SABRIL.

For example:
- If you are using 1 packet of SABRIL, you will need to use 10 mL of water (fill the 10 mL oral syringe 1 time)
- If you are using 2 packets of SABRIL, you will need to use 20 mL of water (fill the 10 mL oral syringe 2 times)
- If you are using 3 packets of SABRIL, you will need to use 30 mL of water (fill the 10 mL oral syringe 3 times)

Step 6: Use the 10 mL oral syringe to draw up 10 mL of water. To do this, put the tip of the oral syringe all the way into the water in your cup. Then pull the plunger up towards you until the edge of the plunger is at the 10 mL line on the barrel of the oral syringe (see FIG. 2E).

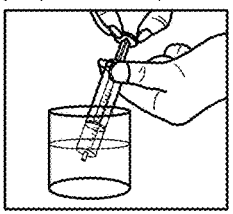

FIG. 2E

- If you see bubbles of air in the oral syringe after drawing up the water, turn the oral syringe so the tip is pointing up (see FIG. 2F). The air will move to the top of the oral syringe. Pull the plunger back towards you and then push it back gently into the oral syringe to get rid of the bubbles. Tiny bubbles are normal.

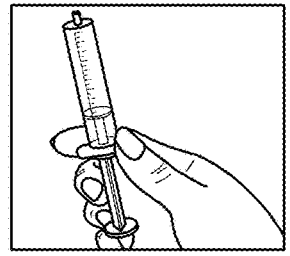

FIG. 2F

Step 7: Check the oral syringe to make sure it is filled with water up to the 10 mL line (see FIG. 2G).

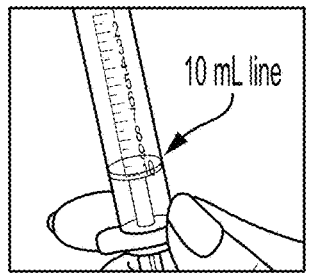

FIG. 9

Step 8: Get the second cup that contains the SABRIL needed for your dose.

Step 9: Hold the 10 mL oral syringe that is filled with water with the tip pointing down over the SABRIL.

Step 10: Slowly push the oral syringe plunger all the way down to empty the water from the oral syringe straight into the cup containing the SABRIL (see FIG. 2H).

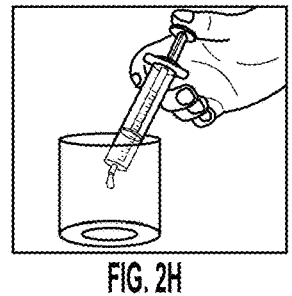

FIG. 2H

Repeat steps 6 through 10 until all of the water that is needed to mix 1 dose of SABRIL has been added to the cup containing the powder.

FIG. 2
CONTINUED

Step 11: Stir the mixture with the small spoon or other clean utensil until the solution is clear (see FIG. 2I). This means that all of the powder is dissolved and ready for use.

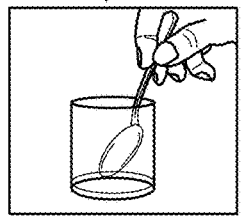
FIG. 2I

- To give a dose of SABRIL to your child, you should use the oral syringe to draw up the total number of mLs of the mixture that your healthcare provider tells you to.
  - If you are giving 3 mL or less of the mixture, use the smaller 3 mL oral syringe.
  - If you are giving more than 3 mL of the mixture, use the larger 10 mL oral syringe (this is the oral syringe that you just used to add the water).

Step 12: Put the tip of the oral syringe all the way into the mixture. Pull the plunger up towards you to draw up the mixture. Stop when the edge of the plunger lines up with markings on the barrel of the oral syringe that matches the number of mLs of mixture your healthcare provider told you to give (see FIG. 2J).

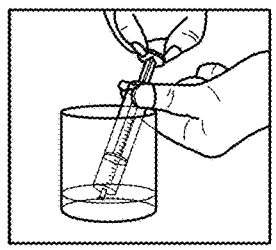
FIG. 2J

- If you see bubbles of air in the oral syringe after drawing up the mixture, turn the oral syringe so the tip is pointing up (see FIG. 2K). The air will move to the top of the oral syringe. Pull the plunger back towards you and then gently push it back in the oral syringe in order to get rid of the bubbles. Tiny bubbles are normal.

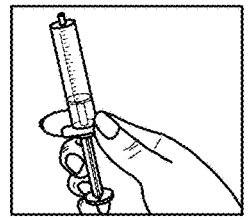
FIG. 2K

Step 13: Place the tip of the oral syringe into your child's mouth and point the oral syringe towards either cheek (see FIG. 2L). Push on the plunger slowly, a small amount at a time, until all of the mixture in the oral syringe is given.

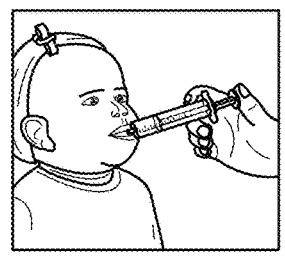
FIG. 2L

- If the dose you are giving your child is more than 10 mLs, repeat steps 12 and 13 until you give the total dose of mixture prescribed by your healthcare provider.

Step 14: Throw away any mixture that is left over. Do not save or reuse any leftover mixture.

Step 15: Wash the oral syringe and mixing cups in warm water. To clean the oral syringes, remove the plunger by gently pulling it straight out of the barrel. The barrel and plunger can be hand washed with soap and water, rinsed, and allowed to dry.

This Instructions for Use has been approved by the U.S. Food and Drug Administration.

Marketed by: Lundbeck, Deerfield, IL 60015, U.S.A.

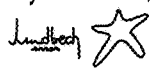

SABRIL is a registered trademark of Lundbeck
Revised: 1/420

FIG. 2 CONTINUED

VIGABATRIN LIQUID PHARMACEUTICAL COMPOSITION

FIELD OF THE INVENTION

The embodiments of the present invention relate to stable vigabatrin pharmaceutical compositions in the liquid form. Particularly, the stable vigabatrin liquid pharmaceutical composition is manufactured as a ready to use premixture that does not require reconstitution or dilution prior to administration to a patient and is stable for at least six months at room temperature.

BACKGROUND OF THE INVENTION

In 2015, 1.2% of the U.S. population had active epilepsy representing about 3.4 million people nationwide (3 million adults and 470,000 children),[1] at an estimated annual cost of $17.6 billion in direct and indirect costs.

Vigabatrin (brand names SABRIL®, VIGADRONER, KIGABEQ®) is an irreversible gamma amino butyric acid (GABA) transaminase inhibitor used as an adjunct therapy to treat refractory complex partial seizures in patients over 2 years of age that are unresponsive to alternative therapies. It may also be used as monotherapy to treat infantile spasms in infants 1 month to 2 years, and infantile spasms in children.

There are only three types of vigabatrin dosage forms currently on the US or the European markets: oral tablets, soluble tablets, and powder for oral solution. Due to the characteristics of the patient population of infants and children, the administration dosage needs to be adjusted. Oral tablets are inconvenient to divide and may be difficult to swallow by the pediatric populations, as well as by patients with swallowing impediments and blockages. Soluble tablets or powder for oral solution can be used for the patients that cannot swallow. However, this method increases the probability of preparation error. The soluble tablet or powder is prepared into a solution with water before administration, and the excess liquid solution must be disposed of immediately. This can lead to incorrect dose preparations, wasted doses, or incorrect reconstitution errors due to non-medical professionals (e.g., patients and caregivers) formulating the wrong concentration of vigabatrin in solution. Administration of incorrect doses of vigabatrin can be fatal or may lead to visual impairment, therefore, the FDA requires vigabatrin to be part of a REMS program. In addition, any excess dose should be discarded as storage of unused powder or reconstituted solutions is not supported by currently approved labels; and any excess powder and solution may contain bacterial contamination or significant degradants if stored for subsequent doses.

Oral liquid dosage forms, including syrups and suspensions are considered favorable types of dosage forms to orally administer medicine to infants and children over tablets, as well as to patients who have difficulty swallowing tablets or capsules. SABRIL® and VIGADRONE® are both available as a white to off-white granular powder for oral solution in packets containing 500 mg vigabatrin, which is dissolved in 10 mL water. Apart from the potential for inaccurate dilution and dosage with the current vigabatrin oral solutions, reconstituted solutions have very limited shelf life and their bitter taste result in low compliance rates, especially in infants and children.

Indeed, the major barrier in development of oral liquid formulations is taste-masking of drugs, as more than 90% of pediatricians in the US reported that a drug's taste and palatability were the greatest barriers to completing treatment.[2] The bitter taste associated with many drugs is thought to have evolved as a deterrent against ingesting toxic substances.[3] In many cases, simple taste-masking is insufficient and more complex formulations are required to encapsulate the drug providing taste-concealing properties. The excipients used in the development of a product need to be safe and acceptable for use in children. Excipients are typically used to optimize the formulation of the medicine to improve palatability, shelf-life and/or manufacturing processes. There are certain excipients that should not be used in children's medicines, as they can retard on-going organ development; or may impact the bioavailability of the drug substance, for example sorbitol, maltitol, or mannitol. It is also important to consider the electrolyte concentration when developing medicines for neonates where renal function may be immature.

Accordingly, there is a need for an industrialized vigabatrin liquid pharmaceutical composition with improved palatability and stable shelf-life, making it overall more acceptable to all types of patient population.

BRIEF SUMMARY OF THE INVENTION

The embodiments of the present invention provide vigabatrin pharmaceutical compositions in the liquid form for oral delivery. These liquid pharmaceutical compositions are manufactured as ready to use premixtures that do not require reconstitution or dilution prior to administration to a patient. These liquid pharmaceutical compositions of the present invention comprise vigabatrin, or a pharmaceutically acceptable salt thereof, in the range from about 0.1 wt % to about 20 wt % and are stable up to at least six months at room temperature or refrigerated conditions. In some embodiments, the liquid pharmaceutical compositions are stable up to at least nine months at room temperature or refrigerated conditions. In some embodiments, the liquid pharmaceutical compositions are stable up to at least 12 months at room temperature or refrigerated conditions. In some embodiments, the liquid pharmaceutical compositions are stable up to at least 15, 18, 21, 24, or 30 months at room temperature or refrigerated conditions. In some embodiments, the liquid pharmaceutical compositions are stable up to at least 36 months at room temperature or refrigerated conditions.

These liquid pharmaceutical compositions have levels of vigabatrin-related compound A and total impurities not more than 0.04% at, or prior to, six months. In some embodiments, the liquid pharmaceutical compositions are packaged in a glass, plastic or metal container; and/or are free of buffering agents, antioxidants, and solubilizers.

The liquid vigabatrin pharmaceutical compositions of the present disclosure further comprise one or more excipients selected from the group of: at least one preservative, at least one sweetener, and/or at least one flavoring agent. In some embodiments, the liquid vigabatrin pharmaceutical composition comprises: at least one preservative, at least one sweetener, and/or at least one flavoring agent. In some embodiments, the liquid vigabatrin pharmaceutical composition comprises: at least one preservative (0.001 to 1.0 wt %), at least one sweetener (0.05 to 40 wt %), and/or at least one flavoring agent (0.001-10.0 wt %). In some embodiments, the liquid vigabatrin pharmaceutical compositions comprise: 0.1125-0.1375 wt % methylparaben, 0.01125-0.01375 wt % propylparaben, 0.225-0.275 wt % sucralose, 0.0027-0.0033 wt % peppermint flavor, and purified water. In some embodiments, the liquid vigabatrin pharmaceutical composition comprises: 0.125 wt % methylparaben, 0.0125 wt % propylparaben, 0.25 wt % sucralose, 0.003 wt % peppermint flavor, and purified water. In some embodiments, the vigabatrin, or a pharmaceutically acceptable salt thereof, is about 10 wt %. In some embodiments, the vigabatrin, or a pharmaceutically acceptable salt thereof, is 10 wt %.

In one embodiment, the present disclosure provides a ready-to-drink vigabatrin liquid pharmaceutical composition comprising: (i) 10 wt % vigabatrin or a pharmaceutically acceptable salt thereof; (ii) 0.125 wt % methylparaben; (iii) 0.0125 wt % propylparaben; (iv) 0.25 wt % sucralose; and (v) 0.003 wt % peppermint flavor, and wherein the liquid pharmaceutical composition does not require reconstitution or dilution prior to administration to a patient and is stable up to at least six months at room temperature and refrigerated conditions. This ready-to-drink vigabatrin liquid pharmaceutical composition is free of buffering agents, antioxidants, and solubilizers, has total impurities no more than 0.04%, has levels of vigabatrin-related compound A no more than 0.04%, and/or is packaged in a glass, plastic or metal container.

In other embodiments, the present disclosure provides methods for the treatment of a condition, which comprises administering to a patient in need thereof a therapeutically effective amount of the ready-to-drink vigabatrin liquid pharmaceutical composition of any of the above-described vigabatrin liquid pharmaceutical compositions in an adult patient or a pediatric patient. The treated conditions include, but are not limited to, refractory complex partial seizures, infantile spasms (aka West's Syndrome), and/or tuberous sclerosis (aka tuberous sclerosis complex, or TSC). In some embodiments, the patient has trouble swallowing a solid oral dosage form or a bitter liquid.

In other embodiments, the present disclosure provides methods for manufacturing a liquid pharmaceutical composition formulated for oral delivery, which comprises the steps of: (i) dissolving preservatives, methylparaben and propylparaben, in 20-95% water at room temperature or elevated temperatures greater than 30° C. by mixing; (ii) dissolving vigabatrin, or a pharmaceutically acceptable salt thereof, by mixing at room temperature, along with at least one preservative, at least one sweetener, and at least one flavoring agent, wherein the order of step (i) and step (ii) can be interchanged; (iii) if required, make up volume quantum satis with purified water and mix to homogeneity; (iv) if required, filter the liquid to remove particulate matter; and (v) transfer the liquid pharmaceutical composition to a suitable primary container and seal it with a suitable closure.

In another aspect of the disclosure, the liquid pharmaceutical composition is compatible with a ketogenic diet for subjects with a subtype of epilepsy, such as refractory complex partial seizures or infantile spasms (aka West's Syndrome). In another aspect of the disclosure, administration of the formulation of the liquid vigabatrin pharmaceutical compositions of the present disclosure improves compliance with the ketogenic diet in a patient with a subtype of epilepsy, such as refractory complex partial seizures or infantile spasms (West's Syndrome). In some embodiments, the feeding of the ketogenic diet and administration of the ready-to-drink vigabatrin liquid pharmaceutical composition is over a period of weeks. In other embodiments, the feeding of the ketogenic diet and administration of the ready-to-drink vigabatrin liquid pharmaceutical composition is over a period of months. The administration of the ready-to-drink vigabatrin liquid pharmaceutical composition can be at the same time, immediately before, or immediately after each meal of the ketogenic diet.

Other implementations are also described and recited herein.

BRIEF DESCRIPTION OF THE DRAWINGS

For the purpose of illustration, certain embodiments of the present invention are shown in the drawings described below. It should be understood, however, that the invention is not limited to the precise arrangements, dimensions, and instruments shown. In the drawings:

FIG. 2 provides the contents of the SABRIL® Instructions for Use Leaflet.

DETAILED DESCRIPTION OF THE INVENTION

Figure 1:
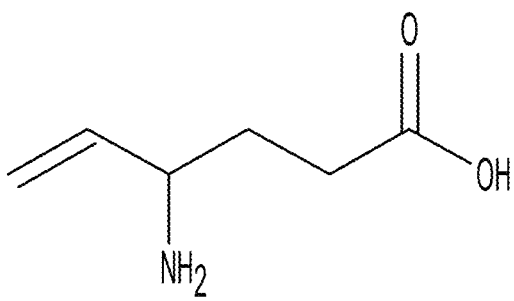
FIG. 1A-B provides the chemical structure and information on vigabatrin (FIG. 1A) and the main vigabatrin impurity, vigabatrin-related compound A (FIG. 1B).
Figure 1:
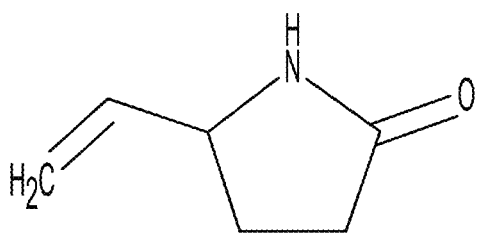

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention. It is to be appreciated that certain aspects, modes, embodiments, variations and features of the invention are described below in various levels of detail in order to provide a substantial understanding of the present invention.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

As used in this specification and the appended claims, the singular forms "a," "an" and "the" include plural referents unless the content clearly dictates otherwise. For example, reference to "a cell" includes a combination of two or more cells, and the like.

As used herein, the term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein the term "industrialized," as in "industrialized vigabatrin liquid pharmaceutical composition," refers to a pharmaceutical composition that is manufactured in a facility using a process approved by a regulatory body and tested prior to releasing a ready-to-use premixture that does not require reconstitution or dilution prior to administration to a patient.

The term "statistically significant" or "significantly" refers to statistical significance and generally means a two-standard deviation (2SD) or greater difference.

As used herein, the terms "subject" or "patient" refer to a mammal, including but not limited to a dog, cat, horse, cow, pig, sheep, goat, chicken, rodent, or primate. Subjects can be house pets (e.g., dogs, cats), agricultural stock animals (e.g., cows, horses, pigs, chickens, etc.), laboratory animals (e.g., mice, rats, rabbits, etc.), but are not so limited. Subjects include human patients. The human subject or patient may be a pediatric, adult, or a geriatric subject. The human subject may be of either sex.

As used herein, the terms "effective amount" and "therapeutically-effective amount" include an amount sufficient to prevent or ameliorate a manifestation of disease or medical condition, such as epilepsy, refractory complex partial seizures, infantile spasms in infants 1 month to 2 years, and infantile spasms in children. It will be appreciated that there will be many ways known in the art to determine the effective amount for a given application. For example, the pharmacological methods for dosage determination may be used in the therapeutic context. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical parameters are improved. Alternatively, treatment is "effective" if the progression of a condition is reduced or halted. That is, "treatment" includes not just the improvement of symptoms or clinical parameters, but also a cessation or at least slowing down of progression or worsening of symptoms that would be expected in the absence of treatment. Beneficial or desired clinical results include, but are not limited to, alleviation of one or more symptom(s), diminishment of extent of the deficit, stabilized (i.e., not worsening) state of epilepsy, refractory complex partial seizures, infantile spasms in infants and children, delay or slowing down of epilepsy and spasms, and an increased lifespan as compared to that expected in the absence of treatment.

As used herein, the term "long-term" administration means that the therapeutic agent or drug is administered for a period of at least 12 weeks. This includes that the therapeutic agent or drug is administered such that it is effective over, or for, a period of at least 12 weeks and does not necessarily imply that the administration itself takes place for 12 weeks, e.g., if sustained release compositions or long acting therapeutic agent or drug is used. Thus, the subject is treated for a period of at least 12 weeks. In many cases, long-term administration is for at least 4, 5, 6, 7, 8, 9 months or more, or for at least 1, 2, 3, 5, 7 or 10 years, or more.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

Unless otherwise defined herein, scientific and technical terms used in connection with the present application shall have the meanings that are commonly understood by those of ordinary skill in the art to which this disclosure belongs.

It should be understood that this invention is not limited to the particular methodology, protocols, animal models, (engineered or genetically modified) cells, organoids, constructs, vectors, carriers, adjuvants, compounds, drug delivery system, antibodies and derivatives, vaccines, and reagents, etc., described herein and as such can vary. The terminology used herein is for the purpose of describing particular embodiments only and is not intended to limit the scope of the present invention, which is defined solely by the claims. Definitions of common terms in immunology and molecular biology can be found in The Merck Manual of Diagnosis and Therapy;[4] The Encyclopedia of Molecular Cell Biology and Molecular Medicine;[5] Molecular Biology and Biotechnology: a Comprehensive Desk Reference;[6] Immunology;[7] Janeway's Immunobiology;[8] Lewin's Genes XI;[9] Molecular Cloning: A Laboratory Manual.;[10] Basic Methods in Molecular Biology;[11] Laboratory Methods in Enzymology;[12] Current Protocols in Molecular Biology (CPMB);[13] Current Protocols in Protein Science (CPPS);[14] and Current Protocols in Immunology (CPI).[15]

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

Tuberous Sclerosis

Tuberous sclerosis (also called tuberous sclerosis complex, or TSC) is a rare, multi-system genetic disease that causes non-cancerous (benign) tumors to grow in the brain and on other vital organs such as the kidneys, heart, eyes, lungs, and skin. The name tuberous sclerosis comes from the characteristic tuber or potato-like nodules in the brain, which calcify with age and become hard or sclerotic. Benign tumors are most common in the brain, kidneys, heart, lungs, and skin. Cancerous tumors are rare in TSC and those that do occur primarily affect the kidneys. TSC occurs in all races and ethnic groups, and in both genders.

The severity of symptoms varies widely. Symptoms range from mild (allowing people to live independent, productive lives) to more severe symptoms that can affect everyday life and even be life-threatening. Many show evidence of the disorder in the first year of life. However, clinical features can be subtle initially, and many signs and symptoms take years to develop. As a result, TSC can be unrecognized or misdiagnosed for years.

Seizures affect most individuals with TSC at some point during their life. While some kinds of seizures caused by TSC result in obvious convulsive movements, others alter awareness, behavior, or postural tone without convulsions. Seizures also can be difficult to control by medication, and sometimes surgery or other measures are used.

Epilepsy

Epilepsy is a condition of the brain marked by a susceptibility to recurrent seizures. There are numerous causes of epilepsy including, but not limited to birth trauma, perinatal infection, anoxia, infectious diseases, ingestion of toxins, tumors of the brain, inherited disorders or degenerative disease, head injury or trauma, metabolic disorders, cerebrovascular accident, and alcohol withdrawal.

There are a large number of subtypes of epilepsy that have been characterized. For example, the most recent classification system adopted by the International League Against Epilepsy's ("ILAE") Commission on Classification and Terminology provides the following list of epilepsy syndromes:[16]

I. Electroclinical syndromes arranged by age at onset:
  A. Neonatal period: 1. Benign familial neonatal epilepsy (BFNE), 2. Early myoclonic encephalopathy (EME), 3. Ohtahara syndrome;
  B. Infancy: 1. Epilepsy of infancy with migrating focal seizures, 2. West syndrome, 3. Myoclonic epilepsy in infancy (MEI), 4. Benign infantile epilepsy, 5. Benign familial infantile epilepsy, 6. Dravet syndrome, 7. Myoclonic encephalopathy in nonprogressive disorders;
  C. Childhood: 1. Febrile seizures plus (FS+) (can start in infancy), 2. Panayiotopoulos syndrome, 3. Epilepsy with myoclonic atonic (previously astatic) seizures, 4. Benign epilepsy with centrotemporal spikes (BECTS), 5. Autosomal-dominant nocturnal frontal lobe epilepsy (ADNFLE), 6. Late onset childhood occipital epilepsy (Gastaut type), 7. Epilepsy with myoclonic absences, 8. Lennox-Gastaut syndrome, 9. Epileptic encephalopathy with continuous spike-and-wave during sleep (CSWS), 10. Landau-Kleffner syndrome (LKS), 11. Childhood absence epilepsy (CAE);
  D. Adolescence-Adult: 1. Juvenile absence epilepsy (JAE), 2. Juvenile myoclonic epilepsy (JME), 3 Epilepsy with generalized tonic—clonic seizures alone, 4. Progressive myoclonus epilepsies (PME), 5. Autosomal dominant epilepsy with auditory features (ADEAF), 6. Other familial temporal lobe epilepsies;
  E. Less specific age relationship: 1 Familial focal epilepsy with variable foci (childhood to adult), 2. Reflex epilepsies;
II. Distinctive constellations:
  A. Mesial temporal lobe epilepsy with hippocampal sclerosis (MTLE with HS);
  B. Rasmussen syndrome;
  C. Gelastic seizures with hypothalamic hamartoma;
  D. Hemiconvulsion—hemiplegia—epilepsy;
  E. Other epilepsies, distinguished by 1. presumed cause (presence or absence of a known structural or metabolic condition, then 2. primary mode of seizure onset (generalized vs. focal);
III. Epilepsies attributed to and organized by structural-metabolic causes:
  A. Malformations of cortical development (hemimegalencephaly, heterotopias, etc.);
  B. Neurocutaneous syndromes (tuberous sclerosis complex, Sturge-Weber, etc.);
  C. Tumor, D. Infection, E. Trauma;
IV. Angioma:
  A. Perinatal insults, B. Stroke, C. Other causes;
V. Epilepsies of unknown cause.
VI. Conditions with epileptic seizures that are traditionally not diagnosed as a form of epilepsy per se:
  A. Benign neonatal seizures (BNS); and B. Febrile seizures (FS).

As can be seen from, for example, Part V of that list, there are still subtypes of epilepsy that have not yet been fully characterized and thus, the list is far from complete.

Infantile Spasms

Infantile spasms (IS), also known as West's Syndrome, are the defining seizures of West syndrome, an early life epilepsy (ELE) associated with refractory seizures, severe developmental consequences and early mortality. The spasms look like a sudden stiffening of muscles; and the baby's arms, legs, or head may bend forward. The seizures occur in a series of short spasms, about one to two seconds in length. Babies may have as many as 100 spasms a day. Spasms may be more likely to happen just as the baby is waking up. Additionally, West syndrome involves developmental delay although this feature is not necessarily present from the outset.

Diagnosis and Screening: Infantile spasms are typically diagnosed by hypsarrhythmia, a specific electrographic signature that manifests as a highly chaotic pattern characterized by multifocal spikes and high voltage slow waves identified during an electroencephalogram (EEG), although other EEG patterns may also be associated with infantile spasms. Evaluation of EEG patterns when the child is awake, asleep, or experiencing a spasm may be used to confirm a diagnosis of infantile spasms.

Treatment: Infantile spasms most often begin between 2 and 9 months but can present up to age 2 years. Later onset spasms may also occur but are rare. Early diagnosis and treatment of infantile spasms may help to lessen developmental issues. Infantile spasms require specific medications such as vigabatrin to stop the spasms.

Reasons Why Treatment is Needed: Children with Infantile spasms are at risk for development of difficult-to-control epilepsy, intellectual disability, and autism. Early and effective treatment is important in improving the prognosis for these infants, as early responders have better long-term epilepsy and developmental outcomes.

Proposed Indication: Currently, reconstituted solutions of Vigabatrin Powder for Oral Solution prepared by parents are indicated as a monotherapy for Infantile Spasms in infants 1 month to 2 years of age for whom the potential benefits outweigh the potential risk of vision loss. A ready-to-use liquid Vigabatrin Oral Product will maintain this indication.

Although the indication and dosage regimen remain unchanged, the ready-to-use liquid formulation of the present disclosure is superior to the product currently on the market since it eliminates the recurrent potential for the severe risk of dosage errors due to erroneously reconstituted or stored solutions.

Description of the Drug and Rationale for Use

Vigabatrin is a selective and irreversible inhibitor of gamma-aminobutyric acid transaminase (GABA-T), which is the enzyme responsible for the metabolism of the central nervous system (CNS) inhibitory neurotransmitter gamma-aminobutyric acid (GABA). The mechanism of action is dose-dependent inhibition of GABA-T and consequent increased levels of GABA in the CNS.

Vigabatrin is an oral anti-epilepsy drug, which was first approved in the United Kingdom in 1989 and has been approved in over 50 countries. It was subsequently approved in the United States on Aug. 21, 2009, as 500 mg tablets (NDA 022006) and 500 mg Sachets containing Oral Powder for Reconstitution (NDA 020427). It is being sold under the brand name SABRIL®.

The currently approved drug, SABRIL® (vigabatrin) Powder for Oral Solution is filled as a powder into a packet containing 500 mg of Vigabatrin. Each packet must be reconstituted with 10 mL of cold or room temperature water by the parent or healthcare provider immediately prior to administration to produce a solution containing 50 mg/ml of vigabatrin. To obtain the dosage required by the patient, a number of packets may need to be used for each dose. The commercially available product contains no antimicrobial preservatives, and no taste-masking agents to reduce the bitterness associated with the vigabatrin active ingredient.

The vigabatrin pharmaceutical composition of the present disclosure is a superior ready-to-use liquid vigabatrin oral product containing 100 mg vigabatrin per mL that also contains antimicrobial preservatives and taste-masking agents.

Superiority Explanation

Due to the safety profile of vigabatrin products, in the United States, they are available only through a restricted program called the Vigabatrin REMS Program. In addition, the U.S. labeling includes the following Black Box Warnings:

Vigabatrin can cause permanent bilateral concentric visual field constriction, including tunnel vision that can result in disability. In some cases, Vigabatrin may also decrease visual acuity Risk increases with increasing dose and cumulative exposure, but there is no dose or exposure to Vigabatrin known to be free of risk of vision loss.

Risk of new and worsening vision loss continues as long as Vigabatrin is used, and possibly after discontinuing Vigabatrin.

Baseline and periodic vision assessment is recommended for patients on Vigabatrin. However, this assessment cannot always prevent vision damage.

As described above, there is a known safety risk that increases with larger doses and cumulative exposure. To reduce the potential dose and exposure risks due to the complicated preparation procedure requiring multiple preparation steps before each dose, the FDA has only approved Vigabatrin Powder for Oral Solution to be provided to patients if the labeling also includes an Instructions for Use Leaflet for parents that contains detailed preparation and dosing instructions. The contents of the SABRIL® Instructions for Use Leaflet are reproduced and provided in FIG. 2.

Considering that currently each solution must be prepared by the parent two times daily immediately before use, at the time that it is dosed to the child, the solutions prepared and provided to the child using the currently marketed product will not have undergone product quality testing. As such, the ready-to-use formulations of the present disclosure are superior to the product currently on the market since it eliminates the recurrent potential for the severe risk of dosage errors due to erroneously reconstituted or stored solutions.

Risks Associated with the Currently Approved Product

Even with the directions provided in the SABRIL® Instructions for Use Leaflet, parents must navigate a complicated preparation procedure that is associated with the following risks:

RISK 1—Materials: As depicted in FIG. 2, preparation of the vigabatrin solution requires the parent to have access to all (>8) of the following materials to properly reconstitute and prepare the product for dosing:

The number of packets of vigabatrin powder for oral solution needed for each dose.

Two clean cups: 1 for mixing and 1 for water. The cup used for mixing Vigabatrin Powder for Oral Solution should be clear so that the parent can see if the powder is dissolved.

Cold or room temperature water to mix with the vigabatrin powder.

One small 3 mL oral syringe and one large 10 mL oral syringe which are provided by the pharmacy.

Small spoon or other clean utensil to stir the mixture.

Scissors.

While these materials may be readily available at home, during travel it may be difficult to remember to bring or to obtain all the listed items. The lack of any of the items may result in postponement or omission of the needed dose. In addition, substitutions of other items for those specified may result in exposure to the powder, inability to verify the complete dissolution of the powder, or difficulty in reconstituting or measuring a correct dose (if any of the syringes are not available).

RISK 2—Volume: The incorrect volume of water may be used to reconstitute the packet. Although the healthcare provider will communicate the appropriate dose of the reconstituted product to the parent, regardless of that dose, the parent must first reconstitute each required packet with 10 ml of water. Prior to dosing the child, the parent must make two independent measurements which could easily result in the preparation of a solution that is not 50 mg/mL as the healthcare provider anticipates. In this instance, there is a real risk that instead of reconstituting each packet with 10 mL of water, the parent may reconstitute the packet with only the amount of water that was intended to be dosed to the patient. This could result in an entire packet being dispensed to the patient, thus potentially leading to a significant overdose.

RISK 3—Incomplete Dissolution: The patient dose may be withdrawn into the dosage syringe prior to full dissolution of the powder. This could lead to higher or lower doses of vigabatrin being provided to the patient than those intended by the labeling or the healthcare provider. This risk is exacerbated if a clear cup is not available at the time of reconstitution.

RISK 4—Incorrect Dosage: The parent may dose the entire solution rather than the amount prescribed. There is a risk that after reconstitution, the entire 10 ml of solution may be dosed to the child, rather than the volume associated with the weight of the child as prescribed by the healthcare provider.

RISK 5—Incorrect Solution: The parent may withdraw the child's dose from the cup containing water rather than from the cup containing the reconstituted solution. There is a risk of an undetected missed dosage if the parent withdraws the child's dose from the cup containing water rather than from the cup containing the reconstituted solution since both the reconstituted solution and water is colorless and odorless. This error would be difficult to detect.

RISK 6—Incomplete/Incorrect Dosage: The child may spit out partial or complete doses of solution. Since the currently available vigabatrin oral solution products do not contain flavoring or sweetening agents, and are used in a pediatric patient population, children may spit-out the bitter solution. If the parent estimates the amount spit-out by the child and attempts to replace it, this may result in an underdosage or overdosage.

RISK 7—Incorrect Syringe/Dosage: The parent may use the incorrect syringe to measure the dosage. Since the parent is provided with a "10-mL reconstitution syringe" and a "3-mL dosage syringe," it is possible that the parent may not understand that the 10-mL reconstitution syringe should not be used for dosing since the markings on the 10-mL syringe may be inadequate to accurately measure smaller doses. If the 10-mL syringe is only intended to measure 10-mL, the pharmacist is not required to provide one with fine graduations.

RISK 8—Contaminants/Degradants: The solution may contain bacterial contamination or significant degradants if the parent stores excess solutions for subsequent doses. Since each packet is diluted with 10 mL, if the child's prescribed dose is less than 10 mL, there is a high risk that leftover solutions may be stored for use later. Based on the patient's prescribed dosage, there is a potential that a large number of "excess doses" may be left over after the solution is prepared. As stated earlier, preparing each dose is time-consuming, and opening a new packet for a dose having discarded a large amount of solution earlier in the day may seem to be unacceptable to parents already experiencing financial strains due to their child's medical condition. Thus, the incentive to use left-over solution may be strong, particularly since many parents would not understand the quality implications of this decision. Since reconstituted solutions of vigabatrin oral powder have not been shown to be stable, there is a risk that the patient may be exposed to unacceptably high levels of impurities on a routine basis. In addition, since the currently-approved formulation does not contain any antimicrobial preservatives, a dose 12, 24, 36 (or more) hours later could support significant microbial growth.

RISK 9—Undiscarded Solution/Dose: The parent may not immediately discard the unused solution after dosage in a safe manner. While it is intended that only the patient be exposed to the drug, there is a risk that a clear solution sitting in a "cup" or other typical mixing vessel may be confused for water or another drink, particularly since the directions require that a cup containing water be in close proximity to that of the reconstituted solution. For children receiving multiple medications, immediate disposal of a clear solution sitting in a cup on the counter may be overlooked. Due to the known hazards associated with the use of this product, this risk is particularly concerning for households with multiple children.

Risks Mitigated by the Proposed Dosage Form

The present disclosure provides a ready-to-use vigabatrin liquid as a 100 mg/ml peppermint-flavored product. It is superior to Vigabatrin Powder for Oral Solution as it addresses the following unmet needs of patients, parents, and healthcare providers:

A. Ready-to-Use Vigabatrin Liquid Formulation: The ready-to-use formulation of the present disclosure eliminates the potential for reconstitution error. In addition, the ready-to-use product is more convenient to patients and eliminates many of the related safety risks associated with the preparation, dosing, and disposal of solutions of Vigabatrin Powder for Oral Use. Accordingly, the ready-to-use product of the present disclosure addresses the above-described RISKS 1, 2, 3, 4, 5, and 9.

B. Concentration: In some embodiments, the concentration of the ready-to-use formulation of the present disclosure is 100 mg/mL whereas the concentration of the reconstituted Vigabatrin Powder for Oral Solution is 50 mg/mL. In addition, the proposed product includes a flavoring agent. As such, since this product is intended to be used by infants, the smaller, more palatable doses are less likely to be spit out, thus reducing the risk of incomplete doses being administered to pediatric patients. In addition, based on physician interviews, a dosage model using a 100 mg/mL product simplifies the dosing discussions with parents since the prescribed dose aligns more intuitively with the volumes required for dosing. Accordingly, the ready-to-use product of the present disclosure addresses the above-described RISK 6.

C. Single Syringe: A single syringe (rather than multiple syringes) will be dispensed by the pharmacist with the ready-to-use formulation of the present disclosure. This will ensure that the parent does not receive a syringe that is not intended for use in patient dosing. Accordingly, the ready-to-use product of the present disclosure addresses the above-described RISK 7.

D. Stability: The ready-to-use formulation of the present disclosure is stable at room temperature, unlike the reconstituted solution which must be used immediately. This ensures that left-over reconstituted solution is not retained and used for multiple subsequent doses, eliminating the potential for microbial contamination and exposure to impurities due to degradation. Accordingly, the ready-to-use product of the present disclosure addresses the above-described RISK 8.

E. Container: The ready-to-use formulation of the present disclosure is contained in a bottle with a child-resistant closure. Since the cap may be replaced immediately after dispensing, the risk of unwanted exposure or poisoning associated with left-over solutions contained in open, unlabeled containers is eliminated. Accordingly, the ready-to-use product of the present disclosure addresses the above-described RISKS 5 and 9.

Risk Assessment

ICH Q9, Quality Risk Management, recognizes that an overall measure of risk is comprised of the severity of consequences of a harmful event, its probability of occurrence, and the detectability of harm prior to an adverse outcome.

Severity: Vigabatrin Powder for Oral Solution must be reconstituted by a parent immediately before use. This preparation requires the parent to follow a complicated procedure that includes multiple preparation steps. See, FIG. 2. Because the FDA recognizes the risks associated with the preparation of vigabatrin powder for Oral Solution, the approved labeling for vigabatrin powder for Oral Solution product includes an Instructions for Use Leaflet for parents. Despite this, each prepared solution provided to the child has a potential to have been prepared incorrectly. As described above, there is a known safety risk that increases with larger doses and cumulative exposure. In addition, there is a known safety risk of seizure if a child is underdosed or misses doses. This risk may be compounded if the parent always prepares the product using the same incorrect method as the overdose or underdose will accumulate over time resulting in an even more severe impact.

Probability: Vigabatrin Powder for Oral Solution product must be prepared by the parent twice daily. Each preparation instance increases the probability of a preparation error.

Detectability: Since each individual solution provided to the child is prepared by the parent immediately before use, the solution dosed to the child will not have undergone product quality testing, and preparation errors are unlikely to be detected prior to providing the reconstituted solution to the child.

In summary, the overall risk associated with the preparation of Vigabatrin Powder for Oral Solution is very high since the product must be prepared by the parent immediately before use twice daily, and since the dose that the child takes is never tested, reconstitution errors will not be detected prior to dosing the solution to the child.

Pharmaceutical Solutions for Oral Dosage

Compared to conventional tablets and capsules, oral liquid dosage forms including solutions, syrups, suspensions, elixirs, and concentrates offer unique advantages to many patients. For example, liquids may provide better patient compliance for those with swallowing difficulties and better dosage control versus a fixed tablet dose. Hence, liquid dosage forms are generally formulated for use in geriatric and pediatric patients. Oral liquids are formulated as solutions, suspensions and emulsions depending on the nature of the active ingredient particularly solubility and stability. They are also designed as ready to use liquids and powders for reconstitution into liquid orals like syrups, solutions, suspensions and emulsions.

The characteristics of active drug are of major concern in developing an oral liquid dosage formulation. The major challenges in developing oral liquid dosage forms are (i) the stability of a drug in solution, (ii) the solubility of a drug at the required level, and (iii) an acceptable taste. It is the effective use of excipients, which allows formulators to overcome these challenges. Additionally, an excipient's compatibility with a drug in the solid state cannot infer the same compatibility in solution.

The decision to develop a solution, syrup or a suspension of a drug is influenced by many factors like solubility and the desired release profile of the drug and properties of the base vehicle, such as surface tension, viscosity, boiling point, and specific heat of solution, all of which may be affected in various ways. In case of clear liquids, lack of solubility of the drug in the base vehicle may demand the need for miscible co-solvents. Similarly, a miscible solvent may be needed to decrease the solubility of the drug in a primary vehicle in formulating a suspension.

The therapeutic utility of drugs involves the application of dosage forms/delivery systems, which serve as carrier systems together with several excipients to deliver the active therapeutic agent to the site of action. Suspensions are an important class of pharmaceutical dosage forms that may be given by many routes, including oral, topical, parenteral, and also used in the eye for ophthalmic purposes. The suspension dosage form has long been used for poorly soluble active ingredients for various therapeutic indications. Surprisingly, large proportions of new drug candidates that are emerging are predominantly water insoluble and, therefore, demonstrate poor bioavailability in the solution dosage form. While suspensions present a viable formulation option for many drugs, particularly for water insoluble, hydrophobic drug substances, there are certain criteria that a well-formulated suspension should meet. Pharmaceutical solutions, where the active pharmaceutical ingredient is soluble offer certain advantages, including stability, uniformity in dosing, etc. Thus, more and better pharmaceutical solution platforms are desirable.

But getting the active pharmaceutical ingredient in solution is only one of the concerns for oral solutions. There are a number of other equally critical "challenges" surrounding the formulation and development of these forms. Liquid formulation needs various excipients including vehicle, solubilizer, stabilizer, and viscosity builder, preservatives, sweeteners, coloring agents and flavoring agents. The selection of these excipients is of major concern to design stable, effective and palatable oral liquid formulation. As mentioned above, the major barrier in development of oral liquid formulations is taste-masking of drugs, as more than 90% of pediatricians in the US reported that a drug's taste and palatability were the greatest barriers to completing treatment.[17] The bitter taste associated with many drugs is thought to have evolved as a deterrent against ingesting toxic substances.[18] In many cases, simple taste-masking is insufficient and more complex formulations are required to encapsulate the drug providing taste-concealing properties. The excipients used in the development of a product need to be safe and acceptable for use in children. Excipients are typically used to optimize the formulation of the medicine to improve palatability, shelf-life and/or manufacturing processes. There are certain excipients that should not be used in children's medicines, as they can retard on-going organ development; or may impact the bioavailability of the drug substance, for example sorbitol, maltitol, or mannitol. It is also important to consider the electrolyte concentration when developing medicines for neonates where renal function may be immature.

Vigabatrin Pharmaceutical Compositions for Oral Dosage

There have been some recent attempts at producing ready-to-drink vigabatrin oral solutions that do not require reconstitution or dilution by the end-user. WO 2020039262 describes pharmaceutical compositions in the form of a solution for oral delivery comprising an active pharmaceutical ingredient, a buffering agent, and water. In some embodiments, the active pharmaceutical ingredient is vigabatrin. Stability was limited to three months. WO 2020155507 also describes a vigabatrin liquid pharmaceutical composition for oral delivery. In addition to vigabatrin, the liquid pharmaceutical composition comprises one or more buffering agent, preservative, antioxidant, and solubilizer, as well as sweetening agent, flavoring agent, and/or suspending agent. Stability was limited to two months. Finally, the ready-to-drink vigabatrin oral solutions described in WO 2020039262 and WO 2020155507 had significant levels of impurities, including a major degradant of vigabatrin, Vigabatrin-related compound A. See, FIG. 1.

As such, these recent attempts have failed to produce vigabatrin liquid pharmaceutical composition for oral delivery with a suitable shelf life of more than 2-3 months, with low levels of impurities. The present disclosure provides vigabatrin liquid pharmaceutical composition for oral delivery that are manufactured as a ready-to-use premixture that do not require reconstitution or dilution prior to administration to a patient and are stable up to six months at room temperature and have impurities and Vigabatrin-related compound A of not more than 0.04% at, or prior to, six months, representing a significant improvement over the ready-to-drink vigabatrin oral solutions described in WO 2020039262 and WO 2020155507. See, Table 3 and Table 4.

In one embodiment, the ready-to-drink vigabatrin oral formulation of the present disclosure contains vigabatrin; at least one preservative; at least one sweetener; at least one flavoring agent; and/or purified water.

In some embodiments, vigabatrin is present in the ready-to-drink vigabatrin oral formulation of the present disclosure in an effective amount from about 1 mg/mL to about 350 mg/mL, about 1 mg/mL to about 300 mg/mL, about 1 mg/mL to about 250 mg/mL, about 1 mg/mL to about 200 mg/mL, about 1 mg/mL to about 150 mg/mL, about 1 mg/mL to about 100 mg/mL, about 1 mg/mL to about 50 mg/mL, about 1 mg/mL to about 25 mg/mL, about 1 mg/mL to about 20 mg/mL, about 1 mg/mL to about 15 mg/mL, about 1 mg/mL to about 10 mg/mL, or about 1 mg/mL to about 5 mg/mL, and values in-between any of these ranges. Specific examples include about 1 mg/mL, about 10 mg/mL, about 12 mg/mL, about 14 mg/mL, about 16 mg/mL, about 18 mg/mL, about 20 mg/mL, about 22 mg/mL, about 25 mg/mL, about 27 mg/mL, about 30 mg/mL, about 40 mg/mL, about 50 mg/mL, about 60 mg/mL, about 70 mg/mL, about 80 mg/mL, about 90 mg/mL, about 100 mg/mL, about 150 mg/mL, about 200 mg/mL, about 250 mg/mL, about 300 mg/mL, or about 350 mg/mL.

In some embodiments, vigabatrin is present in the ready-to-drink vigabatrin oral formulation of the present disclosure in an effective amount from about 0.1 wt % to about 50 wt %, about 0.1 wt % to about 40 wt %, about 0.1 wt % to about 30 wt %, about 0.1 wt % to about 20 wt %, about 0.1 wt % to about 10 wt %, about 0.1 wt % to about 5 wt %, about 0.1 wt % to about 3 wt %, or about 0.1 wt % to about 1 wt %, or any of the values between these ranges. Specific examples include 0.1 wt %, 0.5 wt %, about 1 wt %, about 2 wt %, about 3 wt %, about 5 wt %, about 10 wt %, about 15 wt %, about 20 wt %, about 25 wt %, about 30 wt %, about 35 wt %, about 40 wt %, about 45 wt %, or about 50 wt %. In some embodiments, the weight percentages disclosed herein may be volume-to-volume or weight-to-volume percentages.

In some embodiments, vigabatrin is present in the ready-to-drink vigabatrin oral formulation of the present disclosure in an effective amount from above 1 wt %, at least above 2 wt %, at least above 3 wt %, at least above 4 wt %, at least above 5 wt %, at least above 6 wt %, at least above 7 wt %, at least above 8 wt %, at least above 9 wt %, or at least above 10 wt %.

In some embodiments, the ready-to-drink vigabatrin oral formulation of the present disclosure surprisingly comprises high concentration of vigabatrin, such as about 5 wt %, about 6 wt %, about 7 wt %, about 8 wt %, about 9 wt %, about 10 wt %, about 15 wt %, or about 20 wt %.

In some embodiments the ready-to-drink vigabatrin oral formulation of the present disclosure comprises preservatives. Preservatives are compounds which are included in the compositions to prevent the growth of microorganisms during the product's manufacture and shelf life. Examples of the suitable preservatives are, but not limited to, benzyl alcohol, chloro-butanol, chloro-cresol, alkyl esters of parabens, phenol, phenyl ethanol, benzoic acid, potassium sorbate, sodium benzoate and antimicrobial solvents like propylene glycol, chloroform, or a combination thereof. In some embodiments, the composition comprises at least one preservative selected from methylparaben, propylparaben, or a combination thereof. Preservatives may be present in the composition from about 0.001 wt % to about 1 wt % of the total composition, about 0.001 wt % to about 0.5 wt % of the total composition, about 0.001 wt % to about 0.1 wt % of the total composition, or about 0.001 wt % to about 0.01 wt % of the total composition.

In some embodiments the ready-to-drink vigabatrin oral formulation of the present disclosure comprises at least one sweetening agent. Non-limiting examples of sweetening agents that may be present in the composition are glucose, sucralose, maltitol, trehalose, fructose, xylose, dextrose, galactose, tagatose, maltose, sucrose, glycerol, dulcitol, mannitol, lactitol, sorbitol, xylitol, saccharine or the corresponding sodium, potassium or calcium salt, cyclamate or the corresponding sodium or calcium salt, aspartame, acesulfame or the potassium salt thereof, dulcin, ammonium glycyrrhizinate, alitame, inulin, isomalt, neohesperidin dihydrochalcone, thaumatin, or any combinations thereof. Sweetening agents may be present from about 0.01 wt % to about 40 wt % of the total composition, about 0.01 wt % to about 20 wt % of the total composition, about 0.01 wt % to about 10 wt % of the total composition, about 0.01 wt % to about 5 wt % of the total composition, or about 0.01 wt % to about 1 wt % of the total composition.

In some embodiments, the ready-to-drink vigabatrin oral formulation of the present disclosure comprises at least one flavoring agent. Non-limiting examples of flavoring agents that may be present in the composition include synthetic flavor oils and flavoring aromatics and/or natural oils, extracts from plants leaves, flowers, fruits, and so forth and the like or any combinations thereof. These may include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil and the like or any combinations thereof. Also useful as flavors are vanilla, citrus oil, including lemon, orange, grape, lime and grapefruit, and fruit essences, including apple, banana, pear, peach, strawberry, raspberry, cherry, plum, pineapple, apricot, strawberry flavor, tutti-fruity flavor, mint flavor, or any combinations thereof. Solid forms, such as spray dried forms of flavoring agents, may also be useful in the Liquid dosage forms disclosed herein. In some embodiments, the flavoring agent is tutti-fruity flavor. Flavoring agents may be present from about 0.001 wt % to about 5 wt % of the total composition, about 0.001 wt % to about 4 wt % of the total composition, about 0.001 wt % to about 3 wt % of the total composition, about 0.001 wt % to about 2 wt % of the total composition, or about 0.001 wt % to about 1 wt % of the total composition.

In some embodiments, the compositions disclosed herein are aqueous solutions. In some embodiments, the only solvent that is present in the composition is water. The amount of water present in the composition may vary and depend on the presence of other ingredients in the composition. In some embodiments, water is added q.s. to the composition. In some embodiments, water is present in the composition from about 30 wt % to about 90 wt %, about 30 wt % to about 80 wt %, about 30 wt % to about 70 wt %, about 30 wt % to about 60 wt %, about 30 wt % to about 50 wt %, or about 30 wt % to about 40 wt %.

In one embodiment, the ready-to-drink vigabatrin oral formulation of the present disclosure, contains vigabatrin; two preservatives: methylparaben and propylparaben; a sweetener: sucralose; a flavoring agent: frozen peppermint flavor; and purified water.

In another embodiment, the ready-to-drink vigabatrin oral formulation of the present disclosure, contains vigabatrin (0.1 wt % to about 20 wt %); two preservatives: methylparaben (0.1125-0.1375 wt %) and propylparaben (0.01125-0.01375 wt %); a sweetener: sucralose (0.225-0.275 wt %); a flavoring agent: frozen peppermint flavor (0.0027-0.0033 wt %); and purified water.

In another embodiment, the ready-to-drink vigabatrin oral formulation of the present disclosure contains vigabatrin (10 wt %); two preservatives: methylparaben (0.125 wt %) and propylparaben (0.0125 wt %); a sweetener: sucralose (0.25 wt %); a flavoring agent: frozen peppermint flavor (0.003 wt %); and purified water.

In the present disclosure, vigabatrin may be stable in an aqueous solution, as described above. In some instances, the vigabatrin formulation is stable for 6 to 60 months when stored at room temperature or at temperatures ranging from 2° C. to 30° C. In some embodiments, the liquid pharmaceutical compositions are stable up to at least 12 months at temperatures ranging from 2° C. to 30° C. In some embodiments, the liquid pharmaceutical compositions are stable up to at least 15 months at temperatures ranging from 2° C. to 30° C. In some embodiments, the liquid pharmaceutical compositions are stable up to at least 18 months at temperatures ranging from 2° C. to 30° C. In some embodiments, the liquid pharmaceutical compositions are stable up to at least 21 months at temperatures ranging from 2° C. to 30° C. In some embodiments, the liquid pharmaceutical compositions are stable up to at least 24 months at temperatures ranging from 2° C. to 30° C. In some embodiments, the liquid pharmaceutical compositions are stable up to at least 30 months at temperatures ranging from 2° C. to 30° C. In some embodiments, the liquid pharmaceutical compositions are stable up to at least 36 months at temperatures ranging from 2° C. to 30° C. In some embodiments, the liquid pharmaceutical compositions are stable up to at least 40 months at temperatures ranging from 2° C. to 30° C. In some embodiments, the liquid pharmaceutical compositions are stable up to at least 50 months at temperatures ranging from 2° C. to 30° C. In some embodiments, the liquid pharmaceutical compositions are stable up to at least 60 months at temperatures ranging from 2° C. to 30° C.

The formulation may be stored in any container suitable to maintain the stability of the formulation during its shelf life. In some embodiments, the liquid pharmaceutical compositions are packaged in a glass, plastic or metal container; and/or are free of buffering agents, antioxidants, and solubilizers. These liquid pharmaceutical compositions have levels of vigabatrin-related compound A and total impurities not more than 0.04% at, or prior to, six months.

The dose of vigabatrin to be used in a method of the present disclosure can be provided in the form of a kit, including instructions for using the dose in one or more of the methods of the present disclosure. In certain embodiments, the kit can additionally comprise a dosage form comprising one or more co-therapeutic agents.

Ketogenic Diet to Manage Epilepsy

In 1921, the ketogenic diet was utilized to induce the metabolic effects of fasting for the management of seizures.[19] As use of antiepileptic drugs grew, the diet became reserved for use in selected patients. However, in recent decades, treatment centers have been adopting the classic ketogenic diet. The diet consists of an intake of three or four times as much fat as carbohydrates and protein combined.

The ketogenic diet has now become an established alternative for managing intractable epilepsy. In a study by Caraballo et al.,[20] for example, the diet was administered to subjects with Lennox-Gastaut syndrome (LGS), characterized by high seizure frequency and refractoriness to antiepileptic drugs. After 18 months on the diet, 40% of patients placed on the diet had achieved a more than 50% decrease of seizures. The study concluded that the ketogenic diet, particularly the Johns Hopkins protocol, was an effective and well-tolerated option for patients with LGS.

Patients who are on a ketogenic diet often have a wide range of carbohydrate caloric intake and may also be taking several medications. Liquid medications often contain flavoring and sweetening agents which add several grams of carbohydrates to a patient's diet per day. However, the success of the diet depends upon the restriction of carbohydrates to promote ketosis, the metabolic state where ketone bodies in the blood provide energy. The failure to monitor carbohydrate caloric content of medications may disrupt the diet. As such, there is a need to use keto-friendly flavoring and sweetening agents when formulating liquid medication for patients with epilepsy.

According to another aspect of the present disclosure, the subject may be on, or may be starting on, a ketogenic diet. By "on a ketogenic diet" is meant that the patient consumes nutrition in the form of ketogenic meals, such as ketogenic breakfasts, lunches and dinners. The ketogenic diet, comprised mainly of lipid, has been used for the treatment of epilepsy in children, particularly myoclonic and akinetic seizures,[21] and has proven effective in cases refractory to usual pharmacological means.[22]

Since the early 1990's, when research studies and clinical trials in children demonstrated efficacy of a ketogenic diet in drug-resistant patients and particular pediatric epilepsy syndromes, worldwide interest in the use of ketogenic diets to manage drug-resistant epilepsy in adults has been increasing. Approximately 19.5 million people with epilepsy have seizures uncontrolled by medications. There is also general agreement that patients with infantile spasms (aka West syndrome), Lennox-Gaustat syndrome, Dravet syndrome, Angelman syndrome (particularly with the low glycemic index treatment (LGIT)) and myoclonic-astatic epilepsy benefit from a trial of diet therapy once their epilepsy has become refractory to medication.[23,24] Ketogenic diet therapy offers a needed adjunct strategy for management of status epilepticus. It has the potential advantages of working quickly and synergistically with other concurrent treatments, is relatively easy to start, monitor, and maintain in the controlled intensive care unit setting with close follow up, and it does not contribute to hemodynamic instability seen with anesthetic agents used to treat refractory status epilepticus.

Either oral or parenteral administration of free fatty acids or triglycerides can increase blood ketones, provided that carbohydrate and insulin are low to prevent re-esterification in adipose tissue. Rats fed diets comprised of 70% corn oil, 20% casein hydrolysate, 5% cellulose, 5% McCollums salt mixture, develop blood ketones of about 2 MM. Substitution of lard for corn oil raises blood ketones to almost 5 mM. While cellulose is a glucose polymer and thus a carbohydrate, it is not digestible by humans and is not excluded from a ketogenic diet. Non-digestible carbohydrates are often referred to as dietary fiber and are used as bulking agents as well as thickening agents.

An example of a traditional 1500 calorie/day ketogenic diet recommended by the Marriott Corp. Health Care Services, Pediatric Diet Manual, Revised August 1987 as suitable for a 4-6-year-old epileptic child contained from 3:1 to 4:1 g of fat for each g of combined carbohydrate and protein. At each of three meals of the ketogenic diet, the patient must eat 48 to 50 g fat, only 6 g protein and 10 to 6.5 g carbohydrate. In practice, this means that, at each meal, the child must eat the equivalent of 32 g of margarine per day (about ¼ stick) and drink 92 g of heavy cream (about 100 mL), comprised mainly as medium chain length triglycerides. The diet forces the body to metabolize fats instead of carbohydrates for energy, thereby elevating the level of acetoacetate and D-3-hydroxybutyrate in the blood. These compounds are referred to as "ketone bodies," thus the term "ketogenic" is used to describe the diet.

Diet adherence and compliance remain significant barriers to successful ketogenic diet implementation and as well as to adequate controlled assessments of efficacy in the clinic. A meta-analysis of 11 studies of ketogenic diets in adults reported a combined adherence rate of 45% for all types of ketogenic diets, 38% for the classic KD and 56% for the modified Atkins diet (typically composed of a net 10-20 g/day carbohydrate limit—equivalent to a ratio of 1-2:1 of fat to protein and carbohydrates).[25] Similarly, a recent observational study of 139 adult patients treated with ketogenic diets, 48% (67 of 139) discontinued the diet (39%) or were lost after initial follow up (9%) with approximately half of patients citing difficulty with compliance or restrictiveness as the reason for stopping.[26] The brain accounts for approximately 20 percent of glucose consumption in the body and it tightly regulates the energy supply it requires and the ketogenic diet mimics starvation (i.e., being deprived of a source of glucose as an energy source), causing the body to shift into a metabolic state called ketosis (metabolizing fat as the predominant energy source). One cause of non-compliance or abandonment of the ketogenic diet is carbohydrate craving which results from brain signals that cause craving of the foods containing the nutrient perceived as lacking.

Normally, human bodies are fueled by carbohydrates; ingested carbohydrates are broken down into glucose, which is mainly transported and used as energy or stored as glycogen in liver and muscle tissue. When deprived of dietary carbohydrates (usually below 50 g/day for an adult), the liver becomes the sole provider of glucose to feed bodily organs, especially the brain which, as mentioned above, accounts for about 20% of total energy consumption. However, in some patients the perceived energy imbalance results in cravings, sometimes intense, for carbohydrates. In some patients, the cravings subside over time as the body and brain adjust to the new energy balance, however, in other patients the craving for carbohydrates continues. To be successful on a ketogenic diet, a patient must avoid or strictly limit the amount of carbohydrates consumed; the consequence of non-adherence is that the body shifts back to glucose metabolism and the anti-seizure benefits subside, and cravings continue.

The brain maintains a balance between excitation and inhibition which is mediated through two main neurotransmitters, the excitatory glutamate and the inhibitory GABA. Excessive glutamate signaling, which occurs in stroke, seizures and neurodegeneration, results in excitotoxicity. While the exact mechanism of action of the ketogenic diet is not well understood, one long-standing hypothesis is that ketone bodies may act directly as pharmacological agents, although possible targets have not been elucidated. Recently, glutamate transport into synaptic vesicles by the vesicular glutamate transporter, VGLUT2, was found to be inhibited by the ketone body acetoacetate[27] at concentrations that are expected during the ketogenic diet. In cultured neurons exposed to acetoacetate, glutamate release decreased; thus, inhibition of glutamate signaling by acetoacetate may reduce neuronal excitability. Earlier work suggested that increased production of the inhibitory neurotransmitter GABA might result from changes in brain metabolism produced by ketogenic diet. Without being bound to a particular theory, it is hypothesized that glutamate recycling via glutamine becomes more efficient when ketone bodies are available, and that this may improve GABA resynthesis for inhibitory neurotransmission even more than it affects glutamate repackaging for excitatory neurotransmission. The higher GABA production would be expected to increase inhibitory signaling in the brain, though in rodents, elevations in total brain GABA levels have not been observed. Such changes in GABA signaling may complement the hypothesized alteration in glutamate signaling produced by acetoacetate.[28]

In order to be effective for this purpose, however, the patient must strictly observe the diet. Vitamin and mineral supplements are included in the diet to make it nutritionally complete, since the diet is very high in fat, low in proteins, and requires the near elimination of carbohydrates. Each patient's diet is mathematically calculated based on the age, size, and activity level of the patient. Patients normally follow the diet for one to two years, at which time the patient is slowly weaned onto a normal diet. The diet has been found to be particularly effective with epileptic children. Major drawbacks are that the diet is not very palatable, and that patient compliance demands complete commitment on the part of the patient and his or her family. Moreover, the diet's high fat content might increase the risk of vascular diseases, such as atherosclerosis in long-term use.

In the present disclosure, the effective dose of vigabatrin may be administered alone or in combination with a non-pharmacological therapy to a patient with epilepsy or IS. Combination therapeutic methods are methods where a formulation having an effective dose of a compound may be used in combination with an additional therapy. As used herein, a dose of an agent, e.g., vigabatrin, refers to a therapeutically effective dose of the subject formulation containing the agent. The terms "agent," "compound," and "drug" are used interchangeably herein. In one embodiment, a vigabatrin formulation having an effective amount of active agent can be administered alone or in conjunction with a low carbohydrate diet, such as a ketogenic diet. As used herein, an "effective amount" is an amount of a subject compound that, when administered to an individual in one or more doses, in monotherapy or in combination therapy, is effective to reduce the occurrence of seizures by about 20%, at least about 30%, at least about 40%, at least about 50%, at least about 60%, at least about 70%, at least about 80%, or at least about 90%. In some embodiments, the subject method further includes co-administering concomitantly with the ketogenic diet a dose of vigabatrin. In some instances, the method includes administering the compound to a subject, e.g., a patient, on a ketogenic diet. In some embodiments, the method further includes administering a ketogenic diet to a patient.

The terms "co-administration" and "in combination with" include the administration of two or more therapeutic agents or therapies either simultaneously, concurrently or sequentially within no specific time limits. In one embodiment, a therapeutic agent, e.g., an amount of vigabatrin, is present in the subject's body at the same time or exerts a biological or therapeutic effect at the same time as another therapy, e.g., a ketogenic diet. In one embodiment, the therapeutic agent, e.g., an effective dose of vigabatrin, and non-pharmacological therapy, e.g., a ketogenic diet, are administered at the same time. The effective dose of the formulation of vigabatrin may be administered at the same time with a meal of the ketogenic diet. In other embodiments, the therapeutic agent and non-pharmacological therapy are administered at different times. The effective dose of the vigabatrin formulation may be administered, e.g., before or after a meal of the ketogenic diet. In certain embodiments, a first therapeutic agent or a therapy can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent or therapy.

"Concomitant administration" of a therapeutic drug or non-pharmacological therapy means administration of the compound and additional therapy at such time that both the drug and the non-pharmacological therapy of the present invention will have a therapeutic effect. Such concomitant administration may involve concurrent (i.e., at the same time), prior, or subsequent administration of the drug with respect to the administration of a non-pharmacological therapy. A person of ordinary skill in the art would have no difficulty determining the appropriate timing, sequence and dosages of administration for particular drugs or therapies of the present disclosure.

In some embodiments, a subject compound, e.g., vigabatrin, and at least one additional compound or therapy, e.g., a meal of a ketogenic diet, are administered to the subject within twenty-four hours of each other, such as within 12 hours of each other, within 6 hours of each other, within 3 hours of each other, or within 1 hour of each other.

In certain embodiments, the compound and therapy are administered within 1 hour of each other. In certain embodiments, the compound and therapy are administered substantially simultaneously. By administered substantially simultaneously is meant that the compound and therapy are administered to the subject within about 10 minutes or less of each other, such as 5 minutes or less, or 1 minute or less of each other.

A method of the present disclosure can be practiced on any suitable subject. A subject of the present disclosure may be a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

A method of the present disclosure can be practiced on any appropriately diagnosed patient. In a typical embodiment of the present disclosure, the patient is an adult, or is aged about 18 or less, about 16 or less, about 14 or less, about 12 or less, about 10 or less, about 8 or less, about 6 or less or about 4 or less to about 0 months or more, about 1 month or more, about 2 months or more, about 4 months or more, about 6 months or more or about 1 year or more. Thus, the diagnosed patient is typically about one month old or older when treated.

The liquid oral solution dosage form may be suitable for administering a therapeutically effective dose of vigabatrin to a subject based on the condition, sex, and overall disease state of the subject. In some instances, the liquid oral solution dosage form may be suitable for age-based or weight-based dosing. The oral solution dosage form may be suitable for both pediatric and adult populations. In some instances, the oral liquid dosage forms are used by patients who experience difficulty in swallowing.

According to the present disclosure, there is provided a therapeutically effective dose of a formulation containing vigabatrin as the active agent. In some instances, the formulation may include an effective amount of a therapeutic agent suitable for a single administration to provide a therapeutic effect. A therapeutically effective dose may be any variable liquid dose volume that can be measured and administered. In some instances, a range of dose volumes includes volumes suitable for administration to pediatric populations. In certain embodiments, a range of dose volumes includes 0.2 mL to 12 mL, such as, for example, 0.5 mL to 6 mL. In some instances, the dosage volume of the present invention is compatible in carbohydrate caloric content with a ketogenic diet.

The formulation and dosage of the present invention is one that is compatible with a ketogenic diet. In some cases, the total carbohydrate caloric content of a single dose of the formulation ranges from zero to five carbohydrate calories. In certain embodiments, a single component of the subject formulation has a carbohydrate caloric content of zero to two carbohydrate calories. In some embodiments, the formulation lacks a nutritive/digestible/glycemic carbohydrate.

In some embodiments, the formulation is a liquid vigabatrin formulation, comprising a therapeutically effective amount of a vigabatrin active agent; and a pharmaceutically acceptable vehicle, wherein the formulation does not contain a digestible carbohydrate and reduces carbohydrate craving thus promoting compliance with a ketogenic diet.

Some embodiments of the technology described herein can be defined according to any of the following numbered paragraphs:

1. A liquid pharmaceutical composition comprising vigabatrin, or a pharmaceutically acceptable salt thereof, in the range from about 0.1 wt % to about 20 wt %, wherein the liquid pharmaceutical composition:
   (i) is a ready to use premixture that does not require reconstitution or dilution prior to administration to a patient;
   (ii) is stable for at least six months at room temperature or refrigerated conditions.
2. The liquid pharmaceutical composition of paragraph 1, wherein liquid pharmaceutical composition is free of buffering agents, antioxidants, and solubilizers.
3. The liquid pharmaceutical composition of any of paragraphs 1-2, wherein liquid pharmaceutical composition further has levels of vigabatrin-related compound A and total impurities not more than 0.04% at or prior to six months.
4. The liquid pharmaceutical composition of any of paragraphs 1-3, wherein liquid pharmaceutical composition is packaged in a glass, plastic or metal container.
5. The liquid pharmaceutical composition of any of paragraphs 1-4, wherein liquid pharmaceutical composition further comprises one or more excipients selected from the group of: at least one preservative, at least one sweetener, and at least one flavoring agent.
6. The liquid pharmaceutical composition of any of paragraphs 1-5, wherein liquid pharmaceutical composition comprises: 0.1125-0.1375 wt % methylparaben, 0.01125-0.01375 wt % propylparaben, 0.225-0.275 wt % sucralose, 0.0027-0.0033 wt % peppermint flavor, and purified water.
7. The liquid pharmaceutical composition of any of paragraphs 1-6, wherein liquid pharmaceutical composition comprises: 0.125 wt % methylparaben, 0.0125 wt % propylparaben, 0.25 wt % sucralose, 0.003 wt % peppermint flavor, and purified water.
8. The liquid pharmaceutical composition of any of paragraphs 1-7, wherein the vigabatrin, or a pharmaceutically acceptable salt thereof, is about 10 wt %.
9. The liquid pharmaceutical composition of any of paragraphs 1-7, wherein the vigabatrin, or a pharmaceutically acceptable salt thereof, is 10 wt %.
10. A ready-to-drink vigabatrin liquid pharmaceutical composition comprising:
    (i) 10 wt % vigabatrin or a pharmaceutically acceptable salt thereof;
    (ii) 0.125 wt % methylparaben;
    (iii) 0.0125 wt % propylparaben;
    (iv) 0.25 wt % sucralose; and
    (v) 0.003 wt % peppermint flavor,
    wherein the liquid pharmaceutical composition does not require reconstitution or dilution prior to administration to a patient and is stable up to at least six months at room temperature and refrigerated conditions.
11. The ready-to-drink vigabatrin liquid pharmaceutical composition of paragraph 10, wherein the liquid pharmaceutical composition is free of buffering agents, antioxidants, and solubilizers.
12. The ready-to-drink vigabatrin liquid pharmaceutical composition of any of paragraphs 10-11, wherein the liquid pharmaceutical composition has total impurities not more than 0.04% at or prior to six months.
13. The ready-to-drink vigabatrin liquid pharmaceutical composition of any of paragraphs 10-12, wherein liquid pharmaceutical composition further has levels of vigabatrin-related compound A not more than 0.04% at or prior to six months.
14. The ready-to-drink vigabatrin liquid pharmaceutical composition of any of paragraphs 10-13, wherein liquid pharmaceutical composition is packaged in a glass, plastic or metal container.
15. A method for the treatment of a condition, which comprises administering to a patient in need thereof a therapeutically effective amount of the ready-to-drink vigabatrin liquid pharmaceutical composition of any of paragraphs 1-14,
    wherein the condition is refractory complex partial seizures, infantile spasms (aka West's Syndrome), and/or tuberous sclerosis (aka tuberous sclerosis complex, or TSC), and wherein the patient is an adult patient or a pediatric patient.
16. A method for the treatment of a condition, which comprises administering to a patient in need thereof a therapeutically effective amount of the ready-to-drink vigabatrin liquid pharmaceutical composition of any of paragraphs 1-14,
    wherein the condition is refractory complex partial seizures, and wherein the patient is an adult patient or a pediatric patient.
17. A method for the treatment of a condition, which comprises administering to a patient in need thereof a therapeutically effective amount of the ready-to-drink vigabatrin liquid pharmaceutical composition of any of paragraphs 1-14, wherein the condition is infantile spasms (aka West's Syndrome).
18. A method for the treatment of a condition, which comprises administering to a patient in need thereof a therapeutically effective amount of the ready-to-drink vigabatrin liquid pharmaceutical composition of any of paragraphs 1-14, wherein the condition is tuberous sclerosis and wherein the patient is an adult patient or a pediatric patient.
19. The method for the treatment of a condition of any of paragraphs 15-18, wherein the patient has trouble swallowing a solid oral dosage form or a bitter liquid.
20. A method of increasing compliance with a ketogenic diet, comprising the steps of: feeding a ketogenic diet to a patient over a period of days; and administering to the patient over a period of days a ready-to-drink vigabatrin liquid pharmaceutical composition of any of paragraphs 1-14, wherein the patient is diagnosed with refractory complex partial seizures or infantile spasms (West's Syndrome), and wherein the patient is an adult patient or a pediatric patient.
21. The method of increasing compliance with a ketogenic diet of paragraph 20, wherein the feeding of the ketogenic diet and administration of the ready-to-drink vigabatrin liquid pharmaceutical composition is over a period of weeks.
22. The method of increasing compliance with a ketogenic diet of paragraph 20, wherein the feeding of the ketogenic diet and administration of the ready-to-drink vigabatrin liquid pharmaceutical composition is over a period of months.

23. The method of increasing compliance with a ketogenic diet of any of paragraphs 20-22, wherein the administration of the ready-to-drink vigabatrin liquid pharmaceutical composition is at the same time, immediately before, or immediately after each meal of the ketogenic diet.

24. A method of manufacturing a liquid pharmaceutical composition formulated for oral delivery, said method comprising the steps:
   (i) dissolving preservatives, methylparaben and propylparaben, in 20-95% water at room temperature or elevated temperatures greater than 30° C. by mixing;
   (ii) dissolving vigabatrin, or a pharmaceutically acceptable salt thereof, by mixing at room temperature, along with at least one preservative, at least one sweetener, and at least one flavoring agent, wherein the order of step (i) and step (ii) can be interchanged;
   (iii) if required, make up volume quantum satis with purified water and mix to homogeneity;
   (iv) if required, filter the liquid to remove particulate matter; and
   (v) transfer the liquid pharmaceutical composition to a suitable primary container and seal it with a suitable closure.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in drug structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting. Although methods and materials similar or equivalent to those described herein can be used in the practice or testing of this disclosure, suitable methods and materials are described below.

EXAMPLES

The invention now being generally described, it will be more readily understood by reference to the following examples which are included merely for purposes of illustration of certain aspects and embodiments of the present invention and are not intended to limit the invention.

Example 1 Vigabatrin Oral Solution

As discussed above, vigabatrin is available as a white to off-white granular powder for oral solution in packets of 500 mg, which is dissolved in 10 mL water (under the brand names SABRIL® and VIGADRONE®) but these one-time oral solutions require reconstitution and dilution, which can lead to administration errors and have very limited shelf life and their bitter taste result in low compliance rates, especially in infants and children.

Recent attempts at producing ready-to-drink vigabatrin oral solutions, described in WO 2020039262 and WO 2020155507, contain excipients including buffering agents, preservatives, antioxidants, and solubilizers, as well as sweetening agents, flavoring agents, and suspending agents. Although these formulations eliminated the need for reconstitution and dilution, the shelf life was limited to 2-3 months and the formulations had high levels impurities, including a major degradant of vigabatrin, Vigabatrin-related compound A. Furthermore, the added excipients have the potential to alter the oral bioavailability of the ready-to-drink product compared to the currently marketed SABRIL® and VIGADRONE®, or generic products.

The present study had the objective to remove unnecessary excipients to develop a ready-to-drink vigabatrin oral formulation that is comparable to vigabatrin powder for oral solution (marketed as SABRIL® and VIGADRONE® or generics) in terms of viscosity and osmolality in order to have similar pharmacokinetics, while having a shelf life of 6 months or longer. A formulation with lower number of excipients would have the additional benefit of being safer for infants and children.

Development of a Novel Vigabatrin Oral Formulation

The initial basis for modifying the formulation described WO 2020039262 was that the presence of liquid maltitol in the WO 2020039262 formulation had the potential to alter the oral bioavailability of the ready-to-drink product compared to the currently marketed drug (SABRIL® and VIGADRONE®). Stability studies were conducted to evaluate if removal of this excipient would improve overall product quality. Both physicochemical stability and palatability results obtained with formulations without liquid maltitol were comparable or better than formulations containing liquid maltitol. Hence this excipient was removed from future formulations. To balance the sweetness and palatability of the product, sucralose content was increased slightly in the formulations of the present disclosure.

Another key consideration for modifying the formulation described in WO 2020039262 was to produce a ready-to-drink vigabatrin oral formulation that is comparable to SABRIL® and VIGADRONE® in terms of viscosity and osmolality in order to have similar pharmacokinetics profile. Studies with two buffering agents at lower concentrations and without buffers were conducted. The critical quality attributes (CQA) of product without buffering agents were comparable or better than the formulation described WO 2020039262 during stability assessments. See, Table 1. Hence, both buffering agents, sodium dihydrogen phosphate dihydrate and disodium hydrogen phosphate dihydrate, were eliminated from subsequent formulations.

TABLE 1

| Phosphate Buffer system Batch No: | Without phosphate buffer Formula 1 | | At 0.01M Formula 2 | | At 0.005M Formula 3 | |
|---|---|---|---|---|---|---|
| Test parameters | Initial | 3M_25° C./40% RH | Initial | 3M_25° C./40% RH | Initial | 3M_25° C./40% RH |
| Description | Clear colorless solution | Clear colorless solution | Clear colorless solution | Clear colorless solution | Clear colorless solution | Clear colorless solution |
| pH | 6.8 | 6.8 | 6.7 | 6.7 | 6.7 | 6.75 |
| Assay of Vigabatrin | 99.8% | 99.6% | 100.3% | 100.1% | 100.1% | 100.1% |
| Assay of Methyl paraben | 100.2% | 98.9% | 100.4% | 98.9% | 101.2% | 99.5% |
| Assay of Propyl paraben | 100.4% | 98.5% | 94.2% | 92.0% | 99.7% | 97.2% |
| USP related compound A | 0.02% | 0.03% | 0.02% | 0.03% | 0.02% | 0.03% |
| RRT 0.14 | ND* | 0.03% | 0.04% | 0.03% | 0.03% | 0.03% |
| RRT 0.15 | ND | 0.03% | ND | 0.03% | ND | 0.03% |
| RRT 0.16 | 0.03% | ND | 0.03% | ND | 0.04% | ND |
| Total impurities | 0.08% | 0.09% | 0.09% | 0.09% | 0.09% | 0.09% |

*ND = not detected

Critical Quality Attributes

One key consideration for modifying the formulation described in WO 2020155507 was the studies have reporting that a ketogenic diet (KD) can be an effective treatment for children and adults with refractory epilepsy.[29,30] As such, the removal of high carbohydrate sweeteners and replacing these with keto-friendly sweeteners was another objective of the present formulation.

The resulting ready-to-drink vigabatrin oral formulations of the present disclosure contain vigabatrin, along with at least one preservative, a sweetener, a flavoring agent, and purified water, and, importantly, are free of buffering agents, antioxidants, or solubilizers. The formulations are stable for at least 6 months in a suitable container closure system at room temperature or colder and contain less impurities.

The ready-to-drink vigabatrin oral formulation tested in the present study (termed PYR-003 herein) contains vigabatrin (100 mg/mL); two preservatives: methylparaben (1.25 mg/mL) and propylparaben (0.125 mg/mL); a sweetener: sucralose (2.5 mg/mL); a flavoring agent: frozen peppermint flavor (0.03 mg/mL); and purified water. The formulation was prepared according to the protocol provided in Table 2.

TABLE 2

Preparation of PYR-003

| Step 1 | Add 80% of the purified water in stainless steel vessel and heat to 75-80° C. |
| Step 2 | Under continuous stirring, add methylparaben and mix until dissolved. |
| Step 3 | Under continuous stirring, add propylparaben and mix until dissolved. |
| Step 4 | Cool the liquid to about room temperature. |
| Step 5 | Add vigabatrin gradually while stirring. Mix the solution until completely dissolved. |
| Step 6 | Add sucralose and mix until dissolved. |
| Step 7 | Add peppermint flavor and mix uniformly for homogeneity. |
| Step 8 | Make up the volume using purified water. |

In Table 3, the ready-to-drink vigabatrin composition of the present disclosure, PYR-003, is compared to vigabatrin compositions disclosed in WO 2020039262 and in WO 2020155507.

TABLE 3

Comparisons of Ready-to-Drink Vigabatrin Compositions

| Ingredient Category | WO 2020039262 Example 8 | WO 2020155507 Example 1 | WO 2020155507 Example 5 | PYR-003 |
|---|---|---|---|---|
| Vigabatrin | 100 mg/mL (10% w/v) | 50 mg/mL (5% w/v) | 50 mg/mL (5% w/v) | 100 mg/mL (10% w/v) |
| Preservative 1 | Methylparaben, 1.1 mg/mL (0.11% w/v) | Methylparaben ester, 3 mg/mL (0.3% w/v) | Sodium benzoate, 2 mg/mL (0.2% w/V) | Methylparaben, 1.25 mg/mL (0.125% w/v) |
| Preservative 2 | Propylparaben, 0.11 mg/mL (0.011% w/v) | — | — | Propylparaben, 0.125 mg/mL (0.0125% w/v) |

TABLE 3-continued

Comparisons of Ready-to-Drink Vigabatrin Compositions

| Ingredient Category | WO 2020039262 Example 8 | WO 2020155507 Example 1 | WO 2020155507 Example 5 | PYR-003 |
|---|---|---|---|---|
| Buffering agent 1 | Sodium dihydrogen phosphate dihydrate, 1.06 mg/mL (0.106% w/v) | 0.2M phosphate buffer, q.s to 1 mL | 0.2M phosphate buffer, q.s to 1 mL | — |
| Buffering agent 2 | Disodium hydrogen phosphate dihydrate, 0.56 mg/mL (0.056% w/v) | — | — | — |
| Sweetener 1 | Sucralose, 1 mg/mL (0.1% w/V) | Sucrose, 100 mg/mL (10% w/v) | Mannitol, 100 mg/ml (10% w/v) | Sucralose, 2.5 mg/mL (0.25% w/v) |
| Sweetener 2 | Liquid maltitol, 200 mg/mL (20% w/V) | — | — | — |
| Flavoring agent | Frozen peppermint flavor, 0.1 mg/ml (0.01% w/v) | Orange flavor, 1 mg/mL (0.1% w/V) | Strawberry essence, 1 mg/mL (0.1% w/v) | Frozen peppermint flavor, 0.03 mg/mL (0.003% w/v) |
| Antioxidant | — | Proanthocyanidins, 3 mg/mL (0.3% w/v) | Sodium thiosulfate, 1 mg/mL (0.1% w/v) | — |
| Solubilizer | — | Tween 80, 2 mg/ml (0.2% w/v) | Glycerin, 2 mg/mL (0.2% w/v) | — |
| Vehicle/Solvent | Purified water, q.s to 1 mL | Water, 0.5 mL; 0.2M phosphate buffer, q.s. to 1 mL | Water, 0.5 mL; 0.2M phosphate buffer, q.s. to 1 mL | Purified water, q.s to 1 mL |

Abbreviations: quantum satis (q.s.); weight/volume (w/v).

As can be observed in Table 3, the vigabatrin oral formulation of the present disclosure, PYR-003, is the only stable, ready-to-drink vigabatrin composition for oral delivery that is free of buffering agents, antioxidants, and solubilizers, and contains keto-friendly sweetening and flavoring agents.

Removal of these excipients not only produced a ready-to-drink vigabatrin oral formulation that is comparable to SABRIL® and VIGADRONE® in terms of viscosity and osmolality, but this formulation was also found to be more stable for 3 months (data not shown), 6 months (see, Table 4), and longer (data not shown). Importantly, the vigabatrin oral formulation of the present disclosure, PYR-003, was also shown to have less impurities than the formulations described in WO 2020039262 and WO 2020155507, with levels of impurities and vigabatrin-related compound A that are both not more than 0.04% at three months (data not shown) and at six months (see, Table 4).

TABLE 4

Comparisons of Stability and Impurities

| | WO 2020039262 Example 8 | WO 2020155507 Example 1 | WO 2020155507 Example 5 | PYR-003 |
|---|---|---|---|---|
| Stability | 25° C. + 2° C. 40% + 5% RH 3 Months | 25° C. 60% RH 2 Months | 25° C. 60% RH 2 Months | 25° C. + 2° C. 60% + 5% RH 6 Months |
| pH | 6.8 | 6.8 | 6.9 | 6.9 |
| USP, related compound A (RCA) | 0.04% | 0.10% | 0.07% | 0.04% |
| Total impurities | 0.06% | 0.12% | 0.12% | 0.04% |

In conclusion, the present example describes a stable vigabatrin pharmaceutical composition in the form of a solution for oral delivery that is a ready-to-use premixture that does not require reconstitution or dilution prior to administration to a patient and is keto-friendly. This vigabatrin liquid pharmaceutical composition is stable six months or longer at room temperature or refrigerated conditions and has levels of impurities and vigabatrin-related compound A that are both not more than 0.04% at three months and at six months. The compositions of the present disclosure may be advantageous for the patients having swallowing difficulties such as pediatric or geriatric patients or when the patients are unable to take solid oral dosage forms.

REFERENCES

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The foregoing written specification is considered to be sufficient to enable one skilled in the art to practice the present aspects and embodiments. The present aspects and embodiments are not to be limited in scope by examples provided, since the examples are intended as a single illustration of one aspect and other functionally equivalent embodiments are within the scope of the disclosure. Various modifications in addition to those shown and described herein will become apparent to those skilled in the art from the foregoing description and fall within the scope of the appended claims. The advantages and objects described herein are not necessarily encompassed by each embodiment. Those skilled in the art will recognize or be able to ascertain using no more than routine experimentation, many equivalents to the specific embodiments described herein. Such equivalents are intended to be encompassed by the following claims.

[1] CDC Epilepsy Data and Statistics; https://www.cdc.gov/epilepsy/data/index.html.
[2] Milne, C. P. and Bruss, J. B. (2008). "The economics of pediatric formulation development for off-patent drugs." Clin. Ther. 30: 2133-2145.
[3] Glendinning, J. I. (1994). "Is the bitter rejection response always adaptive?" Physiol. Behav. 56: 1217-1227.
[4] THE MERCK MANUAL OF DIAGNOSIS AND THERAPY, (2011). 19th Edition, published by Merck Sharp & Dohme Corp., (ISBN 978-0-911910-19-3).
[5] THE ENCYCLOPEDIA OF MOLECULAR CELL BIOLOGY AND MOLECULAR MEDICINE, Robert S. Porter et al. (eds.), published by Blackwell Science Ltd., 1999-2012 (ISBN 9783527600908).
[6] MOLECULAR BIOLOGY AND BIOTECHNOLOGY: A COMPREHENSIVE DESK REFERENCE, (1995). Robert A. Meyers (ed.), published by VCH Publishers, Inc. (ISBN 1-56081-569-8).
[7] IMMUNOLOGY, (2006). Werner Luttmann, published by Elsevier.
[8] JANEWAY'S IMMUNOBIOLOGY, (2014). Kenneth Murphy, Allan Mowat, Casey Weaver (eds.), Taylor & Francis Limited, (ISBN 0815345305, 9780815345305).
[9] LEWIN'S GENES X I, (2014). published by Jones & Bartlett Publishers (ISBN-1449659055).
[10] Michael Richard Green and Joseph Sambrook, (2012). MOLECULAR CLONING: A LABORATORY MANUAL, 4th ed., Cold Spring Harbor Laboratory Press, Cold Spring Harbor, N.Y., USA (ISBN 1936113414).
[11] Davis et al., (2012). BASIC METHODS IN MOLECULAR BIOLOGY, Elsevier Science Publishing, Inc., New York, USA (ISBN 044460149X).
[12] LABORATORY METHODS IN ENZYMOLOGY: DNA, (2013). Jon Lorsch (ed.) Elsevier (ISBN 0124199542).
[13] CURRENT PROTOCOLS IN MOLECULAR BIOLOGY (CPMB), (2014). Frederick M. Ausubel (ed.), John Wiley and Sons (ISBN 047150338X, 9780471503385).
[14] CURRENT PROTOCOLS IN PROTEIN SCIENCE (CPPS), (2005). John E. Coligan (ed.), John Wiley and Sons, Inc.
[15] CURRENT PROTOCOLS IN IMMUNOLOGY (CPI) (2003). John E. Coligan, ADA M Kruisbeek, David H Margulies, Ethan M Shevach, Warren Strobe, (eds.) John Wiley and Sons, Inc. (ISBN 0471142735, 9780471142737).
[16] Berg, A. T., et. al., (2010). "Revised terminology and concepts for organization of seizures." Epilepsia, 51(4): 676-685.
[17] Milne, C. P. and Bruss, J. B. (2008). "The economics of pediatric formulation development for off-patent drugs." Clin. Ther. 30: 2133-2145.
[18] Glendinning, J. I. (1994). "Is the bitter rejection response always adaptive?" Physiol. Behav. 56: 1217-1227.
[19] Wilder, R., et al., (1921). "The effect of ketogenemia on the course of epilepsy." Mayo Clin. Bull., 2: 307-314.
[20] Caraballo, R. H., et al. (2014). "Ketogenic diet in patients with Lennox-Gastaut syndrome." Seizure, 23(9): 751-755.
[21] Wilder, R., et al., (1921). "The effect of ketogenemia on the course of epilepsy." Mayo Clin. Bull., 2: 307-314.
[22] Freeman, J. M. and Vining, E. P. G. (1992). "Intractable epilepsy." Epilepsia, 33:1132-1136.
[23] Nangia, S., et al., (2012). "Is the ketogenic diet effective in specific epilepsy syndromes?" Epilepsy Res. 100(3): 252-257.
[24] Thibert, R. L., et al., (2012). "Low glycemic index treatment for seizures in Angelman syndrome." Epilepsia, 53(9): 1498-1502.
[25] Ye, F., et al., (2015). "Efficacy of and patient compliance with a ketogenic diet in adults with intractable epilepsy: a meta-analysis." J. Clin. Neurol. 11(1): 26-31.
[26] Williams, T. J. and Cervenka, M. C. (2017). "The role for ketogenic diets in epilepsy and status epilepticus in adults." Clin. Neurophysiol. Pract. 2: 154-160.
[27] Juge, N., et al. (2010). "Metabolic control of vesicular glutamate transport and release." Neuron, 68: 99-112.
[28] Lutas, A. and Yellen, G. (2013). "The ketogenic diet: metabolic influences on brain excitability and epilepsy." Trends Neurosci. 36(1): 32-40.
[29] Thammongkol, S. et al. (2012). "Efficacy of the ketogenic diet: Which epilepsies respond?" Epilepsia, 53(3): e55-e59.
[30] Freeman, J. F. et al. (2009). "A blinded, crossover study of the efficacy of the ketogenic diet." Epilepsia, 50(2): 322-325.

What is claimed is:

1. A ready-to-use liquid oral pharmaceutical composition consisting of:
   about 0.1 wt % to about 20 wt % of vigabatrin or a pharmaceutically acceptable salt thereof;
   about 0.001 wt % to about 1.0 wt % of at least one preservative;
   about 0.01 wt % to about 40.0 wt % of at least one sweetening agent;
   about 0.001 wt % to about 10.0 wt % of at least one flavoring agent; and
   quantum satis (q.s.) purified water;
   wherein the composition is stable for at least six months at temperatures ranging from 2° C. to 30° C., and wherein the total concentration of 5-vinylpyrrolidin-2-one and other impurities is not more than 0.04 wt %.

2. The ready-to-use liquid oral pharmaceutical composition of claim 1, wherein the composition contains from about 1 wt % to about 10 wt % of vigabatrin.

3. The ready-to-use liquid oral pharmaceutical composition of claim 1, wherein the composition contains from about 5 wt % to about 10 wt % of vigabatrin.

4. The ready-to-use liquid oral pharmaceutical composition of claim 1, wherein the composition contains about 100 mg/mL of vigabatrin.

5. The ready-to-use liquid oral pharmaceutical composition of claim 1, wherein the composition contains about 0.001 wt % to about 0.5 wt % of the at least one preservative.

6. The ready-to-use liquid oral pharmaceutical composition of claim 1, wherein the at least one preservative includes methylparaben, propylparaben, or both.

7. The ready-to-use liquid oral pharmaceutical composition of claim 1, wherein the at least one preservative consists of methylparaben and propylparaben.

8. The ready-to-use liquid oral pharmaceutical composition of claim 6, wherein the composition contains about 0.1125 wt % to about 0.1375 wt % of methylparaben.

9. The ready-to-use liquid oral pharmaceutical composition of claim 6, wherein the composition contains about 0.01125 wt % to about 0.01375 wt % of propylparaben.

10. The ready-to-use liquid oral pharmaceutical composition of claim 1, wherein the composition contains about 0.01 wt % to about 5 wt % of the at least one sweetening agent.

11. The ready-to-use liquid oral pharmaceutical composition of claim 1, wherein the sweetening agent includes a sugar or sugar alcohol selected from glucose, maltitol, trehalose, fructose, xylose, dextrose, galactose, tagatose, maltose, sucrose, glycerol, dulcitol, mannitol, lactitol, sorbitol, and xylitol; or a sweetener selected from sucralose, saccharine or a salt thereof, cyclamate or a salt thereof, aspartame, acesulfame or a salt thereof, dulcin, ammonium glycyrrhizinate, alitame, inulin, isomalt, neohesperidin dihydrochalcone, and thaumatin; or a combination thereof.

12. The ready-to-use liquid oral pharmaceutical composition of claim 11, wherein the sweetening agent includes from about 0.01 wt % to about 1 wt % of the sweetener.

13. The ready-to-use liquid oral pharmaceutical composition of claim 1, wherein the composition contains about 0.001 wt % to about 1 wt % of the at least one flavoring agent.

14. A ready-to-use vigabatrin liquid oral pharmaceutical composition consisting of:
about 50 mg/mL to about 150 mg/mL of vigabatrin or a pharmaceutically acceptable salt thereof;
about 0.1125 to about 0.1375 wt % of methylparaben;
about 0.01125 to about 0.01375 wt % of propylparaben;
a sweetening agent;
a flavoring agent; and
water,
wherein the composition is stable for at least six months at temperatures ranging from 2° C. to 30° C., and
wherein the total concentration of 5-vinylpyrrolidin-2-one and other impurities is not more than 0.04 wt %.

15. The ready-to-use liquid oral pharmaceutical composition of claim 14, wherein the sweetening agent is present at a concentration of about 0.01 wt % to about 1 wt %.

16. The ready-to-use liquid oral pharmaceutical composition of claim 14, wherein the flavoring agent is present at a concentration of about 0.001 wt % to about 1 wt %.

17. The ready-to-use liquid oral pharmaceutical composition of claim 14, wherein the liquid pharmaceutical composition consists of:
about 90 mg/mL to about 100 mg/mL of vigabatrin or a pharmaceutically acceptable salt thereof;
about 0.1125 to about 0.1375 wt % of methylparaben;
about 0.01125 to about 0.01375 wt % of propylparaben;
about 0.01 wt % to about 1 wt % of a sweetening agent;
about 0.001 wt % to about 1 wt % of a flavoring agent; and
quantum satis (q.s.) water.

18. The ready-to-use liquid oral pharmaceutical composition of claim 14, wherein the liquid pharmaceutical composition consists of:
about 100 mg/mL of vigabatrin or a pharmaceutically acceptable salt thereof;
about 0.125 wt % of methylparaben;
about 0.0125 wt % of propylparaben;
about 0.01 wt % to about 1 wt % of a sweetening agent;
about 0.001 wt % to about 1 wt % of a flavoring agent; and
quantum satis (q.s.) water.

19. The ready-to-use liquid oral pharmaceutical composition of claim 14, wherein the sweetening agent is a sweetener selected from sucralose, saccharine or a salt thereof, cyclamate or a salt thereof, aspartame, acesulfame or a salt thereof, dulcin, ammonium glycyrrhizinate, alitame, inulin, isomalt, neohesperidin dihydrochalcone, and thaumatin; or a combination thereof.

* * * * *